United States Patent
Moriya et al.

[19]

[11] Patent Number: 6,115,120
[45] Date of Patent: Sep. 5, 2000

[54] SYSTEM AND METHOD FOR DETECTING PARTICLES PRODUCED IN A PROCESS CHAMBER BY SCATTERING LIGHT

[75] Inventors: Tsuyoshi Moriya; Fumihiko Uesugi; Natsuko Ito, all of Tokyo, Japan

[73] Assignee: NEC Corporation, Tokyo, Japan

[21] Appl. No.: 09/413,590

[22] Filed: Oct. 6, 1999

[30] Foreign Application Priority Data

Oct. 8, 1998  [JP]  Japan ................................. 10-301602

[51] Int. Cl.⁷ ..................................................... G01N 21/00
[52] U.S. Cl. .......................... 356/337; 382/145; 356/339
[58] Field of Search ..................................... 356/337, 338, 356/339, 340, 341, 342; 358/343; 382/203, 236, 145; 348/87

[56] References Cited

U.S. PATENT DOCUMENTS 5,946,092  8/1999  DeFreez et al. ........................ 356/336
5,978,078  11/1999  Salamati-Saradh et al. ........... 356/337

OTHER PUBLICATIONS

G. Selwyn, "Plasma Particulate Contamination Control. I. Transport and Process Effects", *Journal of Vacuum Science and Technology*, B, vol. 9, No. 6, Nov./Dec. 1991, pp. 3487–3492.

G. Selwyn et al., "Particle Contamination in a Helicon Plasma Etching Tool", *Journal of Vacuum Science and Technology*, A, vol. 14, No. 2, Mar./Apr. 1996, pp. 649–654.

*Primary Examiner*—Hoa Q. Pham
*Assistant Examiner*—Sang H. Nguyen
*Attorney, Agent, or Firm*—Young & Thompson

[57] ABSTRACT

Particles generated within a semiconductor wafer process chamber are monitored by emitting a rastered laser beam into the process chamber and detecting a two-dimensional image of scattered radiant energy within the process chamber. A video frame representing a matrix array of pixel intensities is produced and processed by a processor. The processor receives first and second video frames, the first frame representing a matrix array of pixels of a background image of the process chamber before a wafer processing is started and the second frame representing a matrix array of corresponding pixels of a target image of the process changer after a wafer processing is started. Differential intensities between the pixels of the background image and corresponding pixels of the target image are detected and a decision is made on the detected intensities to produce an output signal representing presence or absence of the particles.

13 Claims, 7 Drawing Sheets

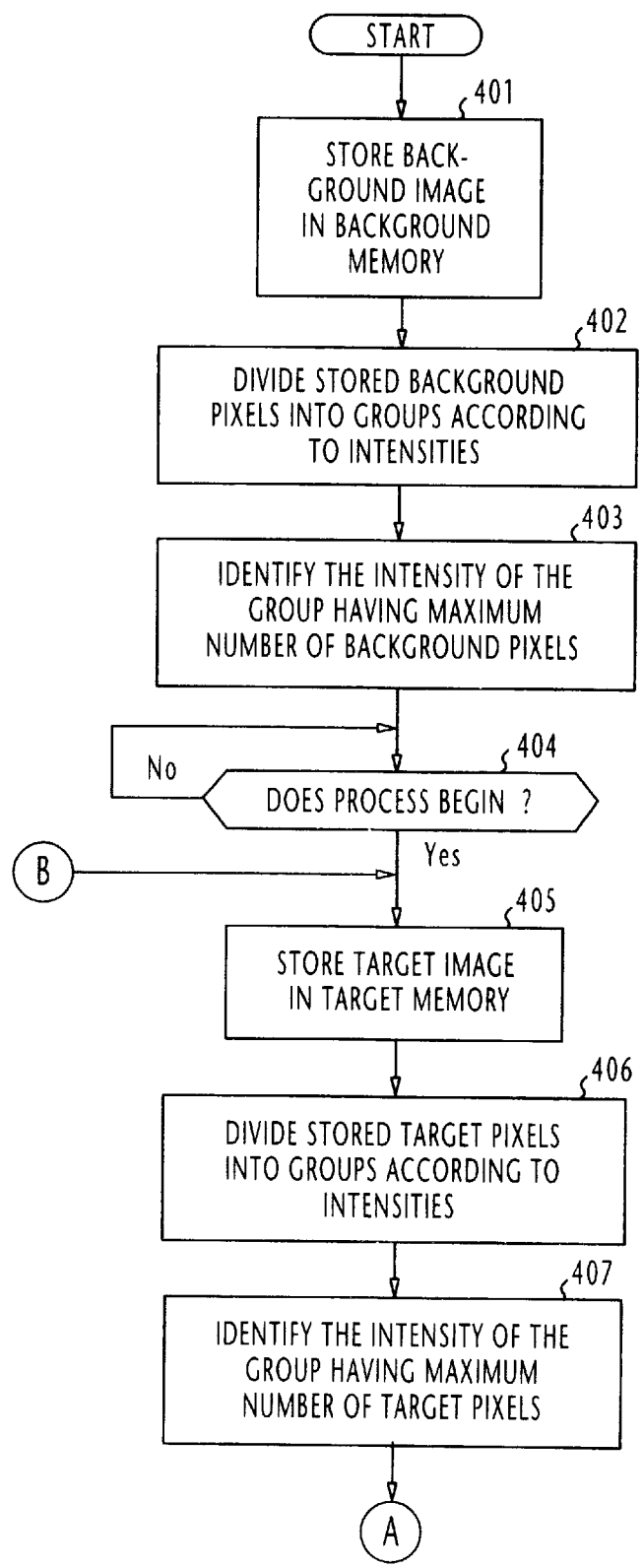

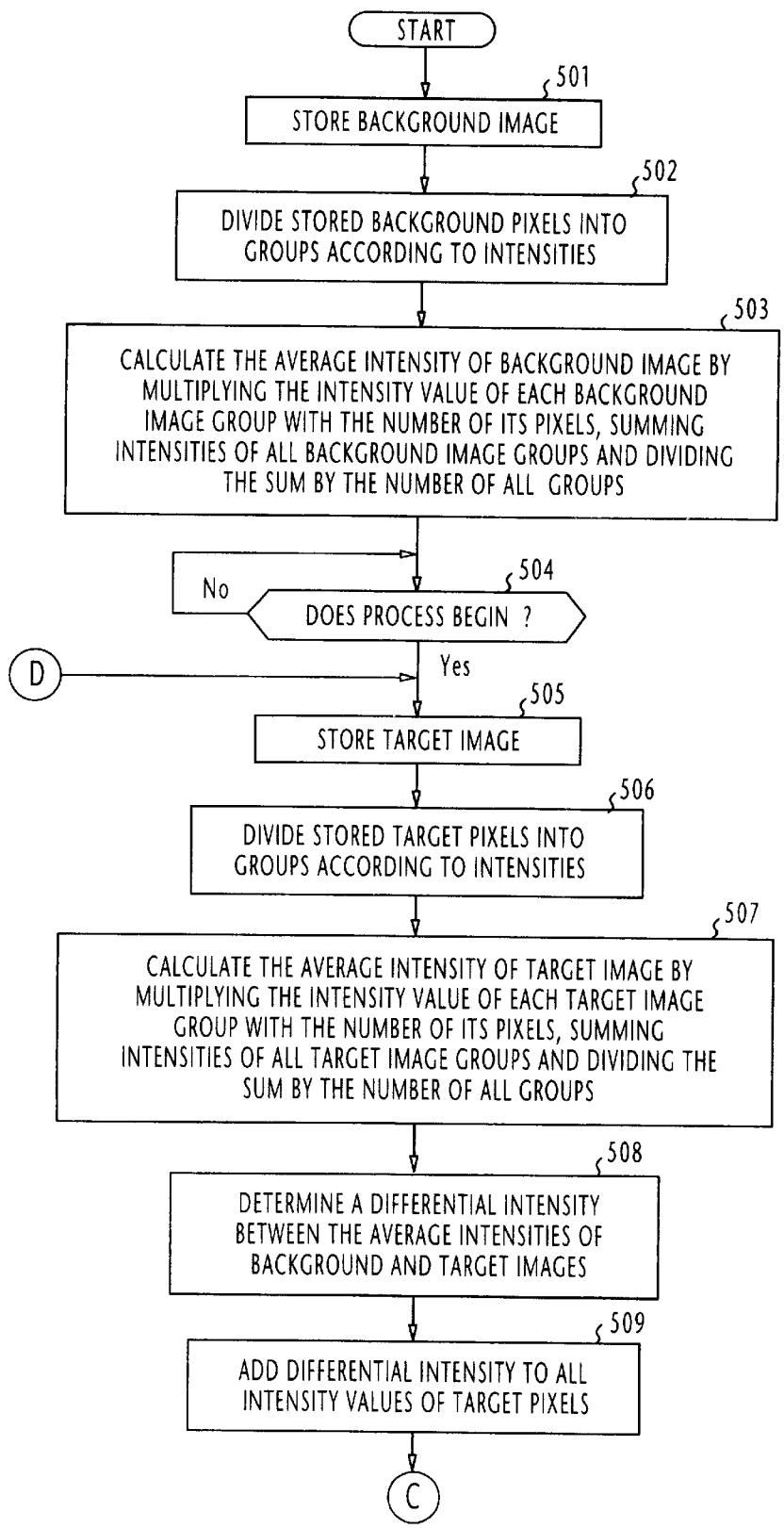

SYSTEM AND METHOD FOR DETECTING PARTICLES PRODUCED IN A PROCESS CHAMBER BY SCATTERING LIGHT

BACKGROUND OF THE INVENTION

1. Field of the Invention

The present invention relates to a system and method for detecting particles produced in a semiconductor process chamber by scattering light.

2. Description of the Related Art

Some of the most common defects of semiconductor wafers are created by particles. The particle may remain on the wafer and be visible as a short circuit between lines or a boulder that the upper layers cannot cover. A particle detection system is described in Journal of Vacuum Science and Technology, B9(6), November/December 1991, pages 3487–3492 and A 14(2), March/April 1996, pages 649–654 (Gay. S. Selwyn). According to this particle detection system a rastered laser beam is injected into a process chamber and light scattered by particles is detected by a CCD camera and displayed on a monitor screen. Because the displayed particles are inspected by human eyes, it takes a long time to determine whether particles are present or not. Another disadvantage of the prior art system is that it lacks precision.

SUMMARY OF THE INVENTION

It is therefore an object of the present invention to provide a system and method for quick and high precision detection of particles produced in a process chamber.

According to the present invention, there is provided a particle detection system for detecting particles generated within a semiconductor wafer process chamber, comprising a radiation source for the emission of radiant energy of visible spectrum into the process chamber, an image sensor for detecting a two-dimensional image of scattered radiant energy within the process chamber and producing therefrom a video frame representing a matrix array of pixel intensities, and a processor connected to the image sensor for detecting differential pixel intensities between a first video frame representing a background image obtained by the image sensor before the process chamber begins a wafer processing and a second video frame representing a target image obtained by the image sensor after the wafer processing is started, and making a decision on the differential pixel intensities to produce an output signal representing presence or absence of the particles.

According to one specific aspect, the processor is arranged to divide the background pixel intensities into a first plurality of groups according to different values of the intensities, divide the target pixel intensities into a second plurality of groups corresponding to the first plurality of groups according to different values of the target pixel intensities, and determine a differential pixel count between the number of pixels contained in each of the first plurality of groups and the number of pixels contained in each corresponding group of the second plurality of groups. The differential pixel intensities are obtained by multiplying the respective intensity of each of the second plurality of groups with the differential pixel count of the group.

According to another aspect of the present invention, the processor is arranged to store the first and second video frames in first and second memories respectively, divide the background pixel intensities stored in the first memory into a first plurality of groups according to different values of the intensities and divide the target pixel intensities stored in the second memory into a second plurality of groups corresponding to the first plurality of groups according to different values of the target pixel intensities, identify the intensity of one of the groups having a maximum number of pixels of background image and identify the intensity of one of the groups having a maximum number of pixels of target image, determine a differential intensity between the identified intensities, add the differential intensity to all target pixel intensities stored in the second memory. The differential pixel intensities are detected from pixel data stored in the first and second memories.

According to a further aspect of the present invention, the processor is arranged to store the first and second video frames in the first and second memories respectively, determine an average intensity of the background pixel intensities stored in the first memory and an average intensity of the target pixel intensities stored in the second memory, determine a differential intensity between the average intensities, and add the differential intensity to all target pixel intensities stored in the second memory. The differential pixel intensities are detected from pixel data stored in the first and second memories.

BRIEF DESCRIPTION OF THE DRAWINGS

The present invention will be described in further detail with reference to the accompanying drawings, in which:

FIGS. 4A and 4B are flowcharts of the operation of the processor according to a third embodiment of the present invention; and FIGS. 5A and 5B are flowcharts of the operation of the processor according to a fourth embodiment of the present invention.

DETAILED DESCRIPTION

Figure 1:
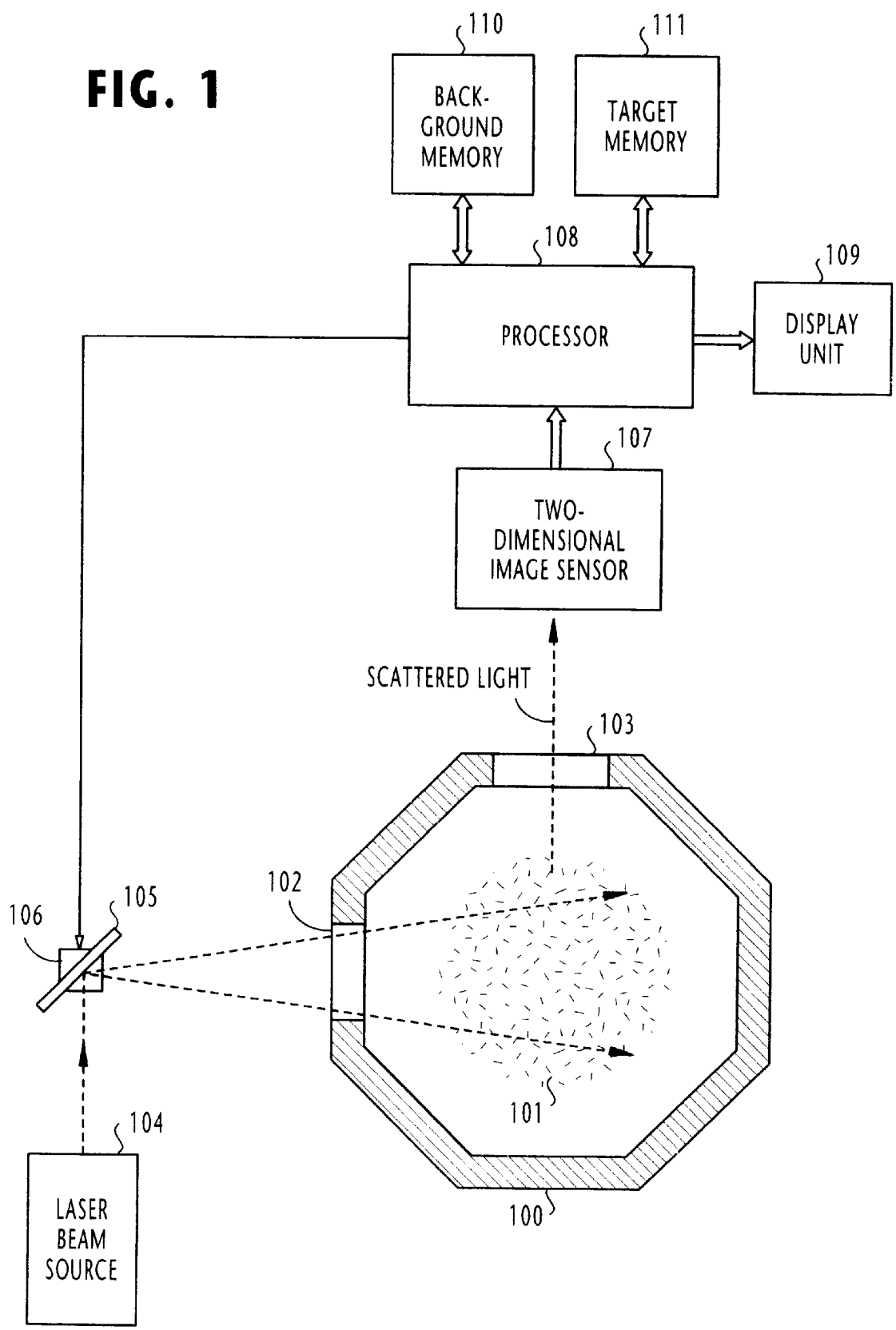
FIG. 1 is a block diagram of a rastered light scattering particle detection system of the present invention.

Referring now to FIG. 1, there is shown a rastered light scattering particle detection system of the present invention. The system includes a process chamber 100 in which a semiconductor wafer is processed in a known manner and, as a result, undesired particles 101 may be produced. Process chamber 100 has a beam injection window 102 and an observation window 103. A laser beam is emitted from a laser beam source 104 toward a scanning mirror 105 which is driven by a scan driver 106 which is controlled by a processor 108, so that the incident beam is deflected in two-dimensional directions to form a rastered scan beam. The rastered scan beam is admitted through the beam injection window 102 into the process chamber 100, where it is scattered off the particles 101. The scattered light is detected through the observation window 103 by a two-dimensional image sensor 107 such as CCD camera. The whole or a selected portion of the area of the camera is converted to a video frame which represents a matrix array of pixels of light intensities, the video frame being supplied to the processor 108.

As described below, the processor 108 processes the video frame and produces results of its decision on a display unit 109 to visually indicate whether particles are present or not. Processor 108 is associated with a background memory 110 and a target memory 111 for purposes of saving a video frame of background image and a video frame of target image, respectively.

The operation of the processor 108 proceeds in a number of ways according to the present invention.

Figure 2:
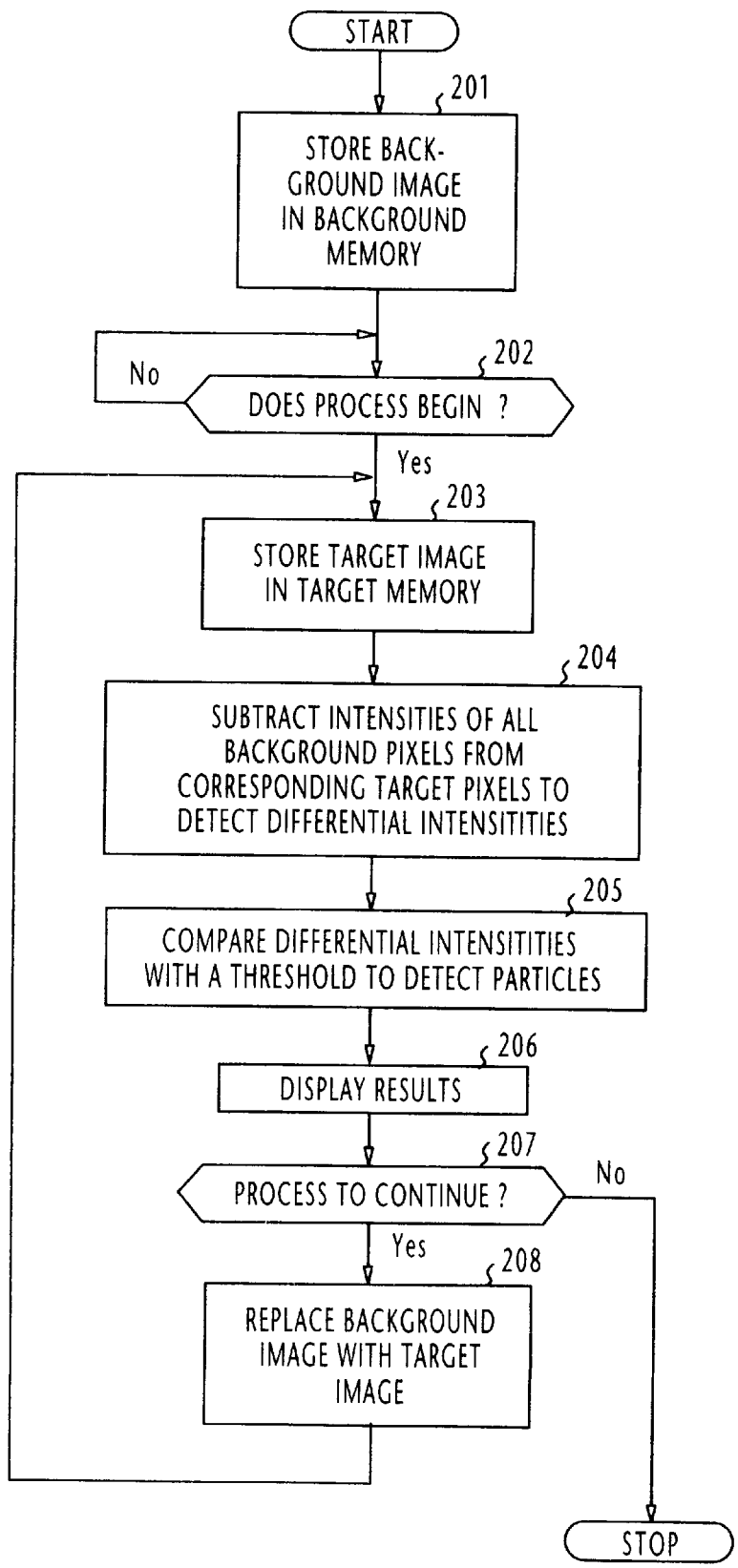
FIG. 2 is a flowchart of the operation of the processor of FIG. 1 according to a first embodiment of the present invention.

According to a first embodiment of the present invention, the processor 108 proceeds according to the flowchart of FIG. 2. The operation of the processor 108 starts with step 201 where the processor receives a video frame from the image sensor 107 representing a rastered background image of the process chamber 100. This background image is obtained by the image sensor 107 before a wafer processing begins in the process chamber 100 by scanning its interior with the rastered laser beam and detecting scattered light from the dark chamber. The video frame of the detected background image is saved in the background memory 110 as a matrix array of background pixel intensities.

When a wafer processing begins in the process chamber 100 (step 202), the processor 108 proceeds to step 203 to receive a rastered target image from the image sensor 107 and stores the received image in the target memory 111 as a matrix array of target pixel intensities. If particles are generated as a result of the wafer processing, the target image contains a trace of such particles. If particles are present, pixel intensities corresponding to the particles in the target memory 111 differ from the corresponding pixel intensities of the background memory 110. At step 204, the processor 108 reads data from both memories 110 and 111 on a pixel-by-pixel basis and subtracts the background pixel intensities from the target pixel intensities to detect differential pixel intensities.

At step 205, the processor 108 compares the differential intensities with a predefined threshold value to determine that particles are present in the process chamber if the threshold value is exceeded. Otherwise, the processor determines that no particles are present. The results of the comparison are visually displayed on the display unit 109 (step 206).

At step 207, the processor 108 checks to see if it continuously perform the above process on a further wafer processing operation. If not, the routine is terminated. Otherwise, the processor proceeds to step 208 to replace the contents of the background memory 110 with those of the target memory 111 and returns to step 203 to repeat the above process.

In this way, particles generated in the process chamber 100 are automatically indicated on the display unit 109 in a shorter time interval and a higher degree of precision than is possible with the conventional visual inspection by operators.

By comparison, the present invention is capable of instantly detecting more than 80 percent of particles, whereas the human inspection takes a period of three seconds to make a decision only on 50 percent of the particles generated.

Figure 3:
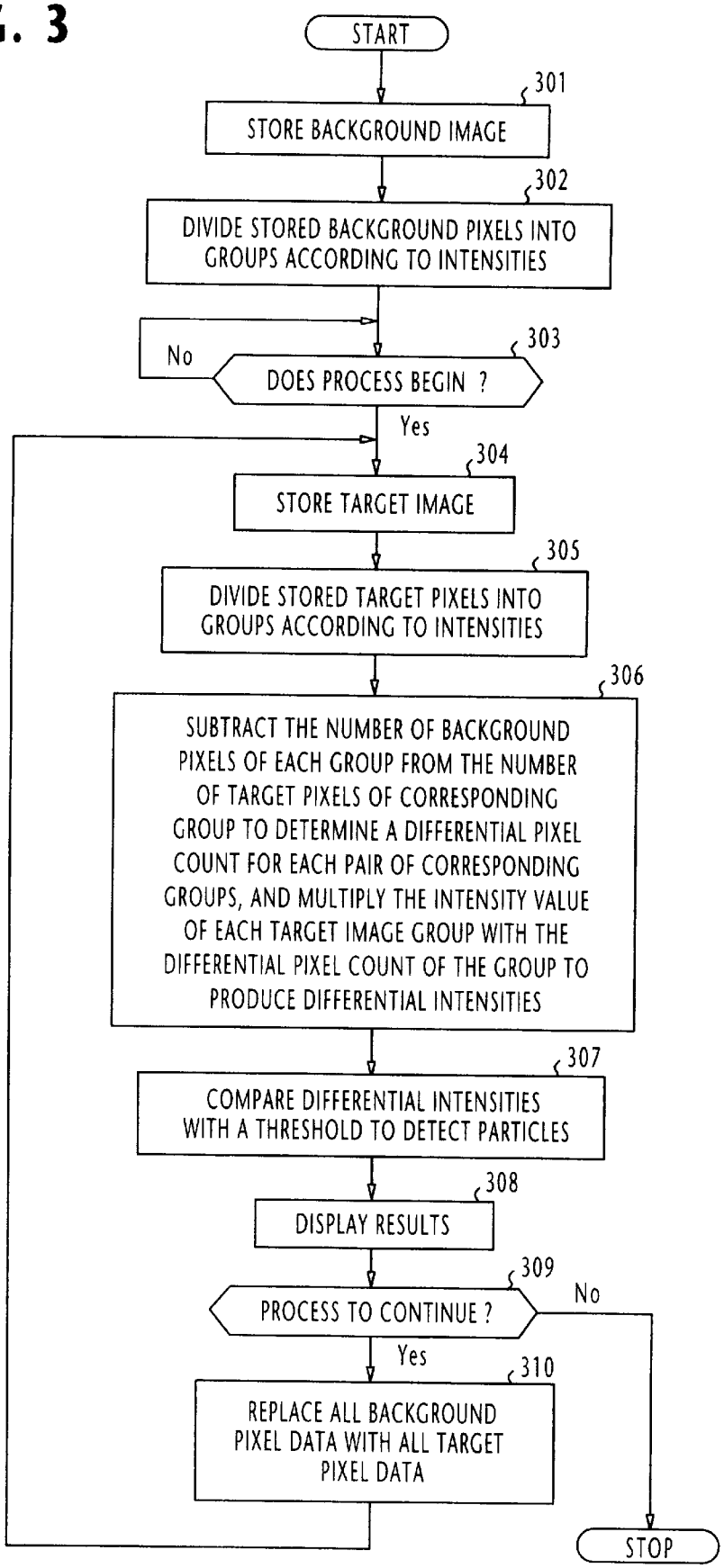
FIG. 3 is a flowchart of the operation of the processor according to a second embodiment of the present invention.

A second embodiment of this invention is shown in FIG. 3. Similar to FIG. 2, the operation of the processor 108 starts with step 301 by storing a rastered background image of the process chamber 100 in the background memory 110 as a matrix array of background pixel intensities and divides the stored pixel data into a predetermined number of groups according to pixel intensities (step 302). Processor 108 proceeds to step 303 to check to see if a wafer processing begins in the process chamber 100. If so, the processor 108 proceeds to step 304 to store a rastered target image from the image sensor 107 into the target memory 111. At step 305, the pixel data in the target memory 111 is divided into the same number of groups according to their intensities.

At step 306, the number of background pixels of each group is subtracted from the number of target pixels of corresponding group to determine a differential pixel count for each pair of corresponding groups. The intensity value of each target image group is then multiplied with the differential pixel count of the group to produce a differential value of intensity for each pair of corresponding groups. Thus, a plurality of differential intensities between the background and target images are obtained.

Similar to the previous embodiments, the presence or absence of particles is determined by comparing the differential intensities with a threshold value (step 307), the results of the comparison are displayed (step 308). If the wafer processing is continued, all pixel data obtained by steps 301 and 302 and stored in the background memory 110 are replaced with corresponding pixel data obtained by steps 304 and 305 and stored in the target memory 111 (step 310). Now, the processor 108 returns to step 304 to repeat the process on the next run.

Figure 4B:
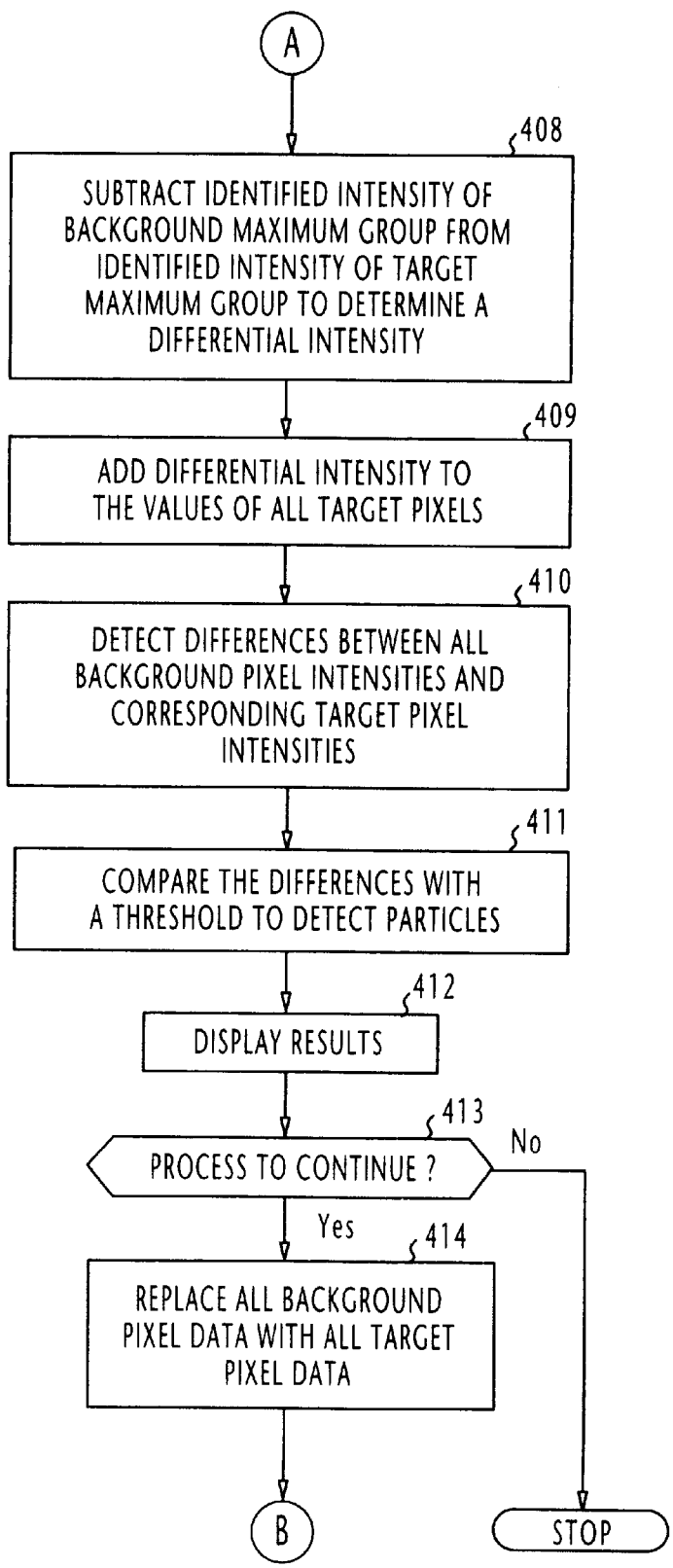

FIGS. 4A and 4B are the flowcharts of the operation of the processor according to a third embodiment of the present invention. The operation of the processor 108 starts with step 401 where the processor stores a video frame from the image sensor 107 in the background memory 110 in the same way as in the previous embodiment.

At step 402, the processor 108 divides the stored background data into a predetermined number of groups according to pixel intensities. At step 403, the processor 108 determines one of the groups having maximum number of background pixels and identifies the intensity of that group.

When a wafer processing begins in the process chamber 100 (step 404), the processor 108 proceeds to step 405 to receive a rastered target image from the image sensor 107 and stores it into the target memory 111.

At step 406, the processor 108 divides the stored target data into the same number of groups as that of the background groups according to pixel intensities. At step 407, the processor 108 determines one of the groups having maximum number of target pixels and identifies the intensity of that target group.

Processor 108 then proceeds to step 408 (FIG. 4B) to subtract the identified intensity of the maximum background group from the identified intensity of the maximum target group to produce a differential intensity.

At step 409, the processor adds the differential intensity to the value of all target pixels. The addition of the differential intensity to the target image has the effect of linearly compensating for the background image of the process chamber.

At step 410, the processor detects differences between all background pixel intensities and corresponding target pixel intensities. The detected pixel-by-pixel intensity differences are compared with a threshold value at step 411 to detect particles. Only if the threshold value is exceeded, it is determined that particles are present in the process chamber. The results of the comparison are displayed at step 412. If there is a next process run (step 413), the pixel data obtained by steps 401, 402 and 403 and stored in the background memory 110 are replaced with corresponding pixel data obtained by steps 405, 406 and 407 and stored in the target memory 111 (step 414). Following the execution of step 414, the processor returns to step 405 to repeat the process on the next run.

Figure 5B:
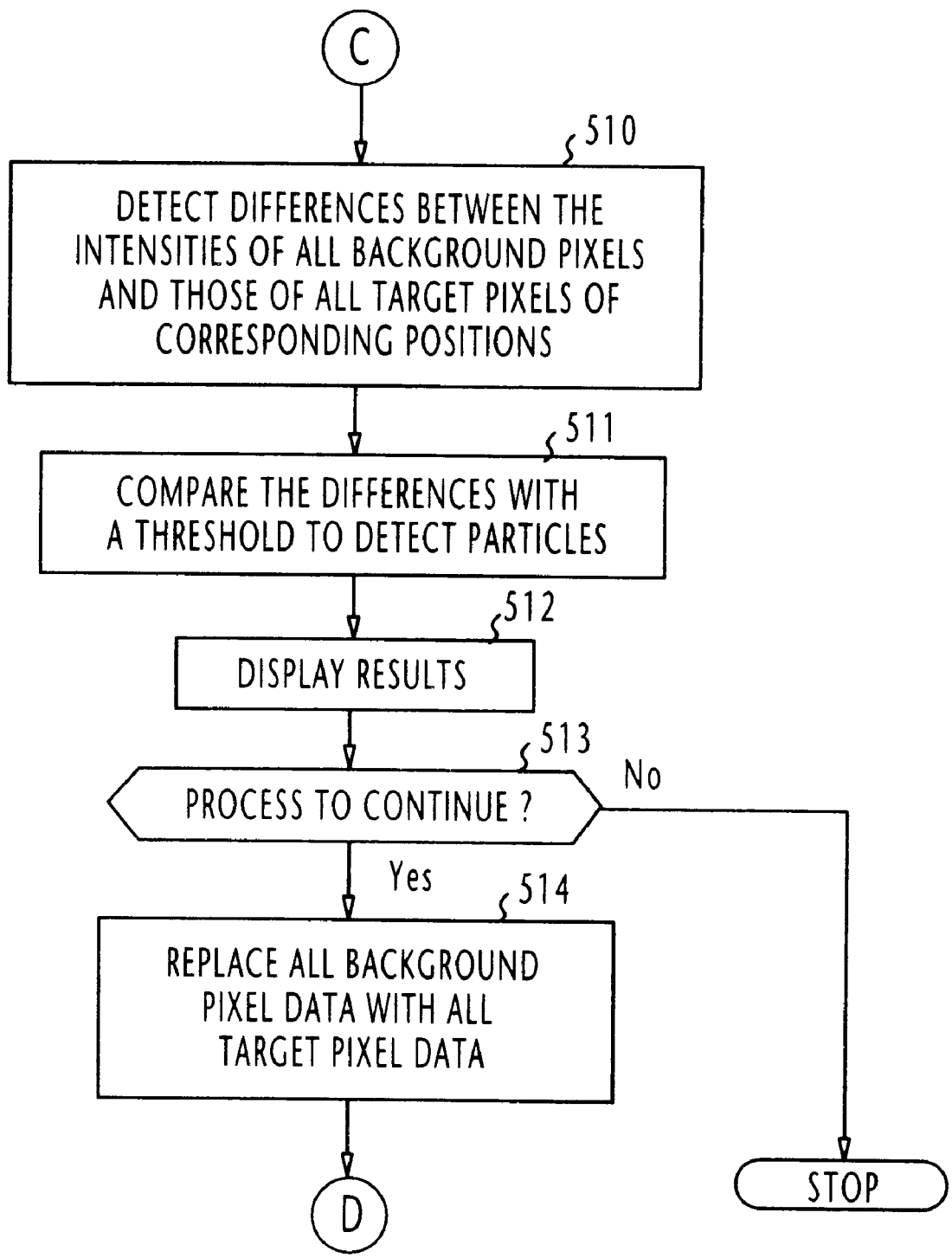

Background image compensation can also be achieved with the use of an average value of background intensities as shown in the flowcharts of FIGS. 5A and 5B.

In FIG. 5A, a background video frame obtained by the image sensor 107 is stored in the background memory 110 (step 501) and the stored pixel values of the background image are divided into groups according to their intensities in the same manner as in the previous embodiments (step 502). At step 503, the average intensity of the background image is calculated by multiplying the intensity value of each background image group with the number of its pixels, summing the multiplied intensity values of all background image groups and dividing the sum by the number of all groups.

When the wafer processing begins (step 504), a target video frame from the image sensor is stored into the target memory 111 (step 505) and the stored pixel values of the target image are divided into groups according to their intensities corresponding to the groups of the background image (step 506). At step 507, the average intensity of the target image is calculated by multiplying the intensity value of each target image group with the number of its pixels, summing the multiplied intensity values of all target image groups and dividing the sum by the number of all groups.

At step 508, a differential intensity between the average intensity of the background image and the average intensity of the target image. The differential intensity is then added to all the intensity values of the target pixels (step 509). Processor 108 then proceeds to step 510 (FIG. 5B) to detect the differences between the intensities of all background pixels and those of the corresponding target pixels. At step 511, the detected intensity differences are compared with the threshold value to detect particles in the process chamber. Results of the comparison are displayed (step 512) and the background pixel data obtained by steps 501, 502 and 503 and stored in stored in the background memory 110 are replaced with the target pixel data obtained by steps 505, 506 and 507 and stored in the target memory 111 (step 514), and steps 505 to 512 are repeated if a subsequent run of wafer processing follows (step 513).

What is claimed is:

1. A particle detection system for detecting particles generated within a semiconductor wafer process chamber, comprising:
   a radiation source for the emission of radiant energy of visible spectrum into said process chamber;
   an image sensor for detecting a two-dimensional image of scattered radiant energy within said process chamber and producing therefrom a video frame representing a matrix array of pixel intensities; and
   a processor connected to said image sensor for detecting differential pixel intensities between a first video frame representing a background image obtained by the image sensor before said process chamber begins a wafer processing and a second video frame representing a target image obtained by the image sensor after said wafer processing is started, and making a decision on said differential pixel intensities to produce an output signal representing presence or absence of said particles,
   wherein said processor is arranged to:
      divide the background pixel intensities into a first plurality of groups according to different values of the intensities,
      divide the target pixel intensities into a second plurality of groups corresponding to the first plurality of groups according to different values of the target pixel intensities,
      determine a differential pixel count between the number of pixels contained in each of said first plurality of groups and the number of pixels contained in each corresponding ground of the second plurality of groups, and
      multiply the respective intensity of each of the second plurality of groups with the differential pixel count of the group to thereby produce said differential pixel intensities.

2. The particle detection system of claim 1, wherein the emitted radiant energy is a rastered laser beam.

3. The particle detection system of claim 1, further comprising a display unit for providing a visual display of said output signal.

4. A particle detection system for detecting particles generated within a semiconductor wafer process chamber, comprising:
   a radiation source for the emission of radiant energy of visible spectrum into said process chamber;
   an image sensor for detecting a two-dimensional image of scattered radiant energy within said process chamber and producing therefrom a video frame representing a matrix array of pixel intensities; and
   a processor connected to said image sensor for detecting differential pixel intensities between a first video frame representing a background image obtained by the image sensor before said process chamber begins a wafer processing and a second video frame representing a target image obtained by the image sensor after said wafer processing is started, and making a decision on said differential pixel intensities to produce an output signal representing presence or absence of said particles; and
   first and second memories, wherein said processor is arranged to:
      store said first and second video frames in said first and second memories, respectively,
      divide the background pixel intensities stored in the first memory into a first plurality of groups according to different values of the intensities and divide the target pixel intensities stored in the second memory into a second plurality of groups corresponding to the first plurality of groups according to different values of the target pixel intensities,
      identify the intensity of one of the groups having a maximum number of pixels of background image and identify the intensity of one of the groups having a maximum number of pixels of target image,
      determine a differential intensity between the identified intensities,
      add the differential intensity to all target pixel intensities stored in said second memory, and
      detect said differential pixel intensities between the background pixel intensities stored in said first memory and corresponding target pixel intensities stored in said second memory.

5. A particle detection system for detecting particles generated within a semiconductor wafer process chamber, comprising:
   a radiation source for the emission of radiant energy of visible spectrum into said process chamber;
   an image sensor for detecting a two-dimensional image of scattered radiant energy within said process chamber and producing therefrom a video frame representing a matrix array of pixel intensities; and
   a processor connected to said image sensor for detecting differential pixel intensities between a first video frame representing a background image obtained by the image sensor before said process chamber begins a wafer processing and a second video frame representing a target image obtained by the image sensor after said wafer processing is started, and making a decision on said differential pixel intensities to produce an output signal representing presence or absence of said particles; and first and second memories, wherein said processor is arranged to:
store said first and second video frames in said first and second memories, respectively,
determine an average intensity of the background pixel intensities stored in the first memory and an average intensity of the target pixel intensities stored in the second memory,
determine a differential intensity between the average intensities,
add the differential intensity to all target pixel intensities stored in said second memory, and
detect said differential pixel intensities between the background pixel intensities stored in said first memory and corresponding target pixel intensities stored in said second memory.

6. A method of detection particles generated within a semiconductor wafer process chamber, comprising the steps of:
a) emitting radiant energy of visible spectrum into said process chamber;
b) detecting a two-dimensional background image of scattered radiant energy within said process chamber before a wafer processing begins and producing a background video frame representing a matrix array of background pixel intensities;
c) detecting a two-dimensional target image of scattered radiant energy within said process chamber after said wafer processing begins and producing a target video frame representing a matrix array of target pixel intensities;
d) detecting differential pixel intensities between the background video frame and the target video frame; and
e) making a decision on said differential pixel intensities to produce an output signal representing presence or absence of said particles.

7. The method of claim 6, further comprising the steps of repeating the steps (c) to (e) by using the target video frame of the step (c) as the background video frame of the step (d), instead of the background video frame previously obtained from the background image of the step (b).

8. A method of detection particles generated within a semiconductor wafer process chamber, comprising the steps of:
a) emitting radiant energy of visible spectrum into said process chamber;
b) detecting a two-dimensional background image of scattered radiant energy within said process chamber before a wafer processing begins and producing a background video frame representing a matrix array of pixels of background intensities;
c) dividing the background pixel intensities into a plurality of groups according to different values of the intensities;
d) detecting a two-dimensional target image of scattered radiant energy within said process chamber after said wafer processing begins and producing a target video frame representing a matrix array of pixels of target intensities;
e) dividing the target pixel intensities into a plurality of groups corresponding to the groups of the step (c) according to different values of the target pixel intensities;
f) subtracting the number of pixels contained in each of said groups of background pixel intensities from the number of pixels contained in each corresponding group of target pixel intensities to determine a differential pixel count and multiplying the respective intensity of each group of the step (e) with the differential pixel count of the group to thereby produce a plurality of differential pixel intensities; and
g) making a decision on said differential pixel intensities to produce an output signal representing presence or absence of said particles.

9. The method of claim 8, further comprising the steps of repeating the steps (d) to (g) by using said each group of target pixel intensities of the step (e) as said each group of background pixel intensities of the step (f), instead of said each group of background video frame previously obtained from the background image of the step (b).

10. A method of detection particles generated within a semiconductor wafer process chamber, comprising the steps of:
a) emitting radiant energy of visible spectrum into said process chamber;
b) detecting a two-dimensional background image of scattered radiant energy within said process chamber before a wafer processing begins and producing a background video frame representing a matrix array of pixels of background intensities;
c) storing said matrix array of background pixel intensities in a first memory;
d) dividing the stored background pixel intensities into a plurality of groups according to different values of the intensities;
e) identifying the intensity of one of the groups of background pixel intensities containing a maximum number of pixels;
f) detecting a two-dimensional target image of scattered radiant energy within said process chamber after said wafer processing begins and producing a target video frame representing a matrix array of pixels of target intensities;
g) storing said matrix array of target pixel intensities in a second memory;
h) dividing the stored target pixel intensities into a plurality of groups corresponding to the groups of the step (d) according to different values of the target pixel intensities;
i) identifying the intensity of one of the groups of target pixel intensities containing a maximum number of pixels;
j) determining a differential intensity between the intensity identified by the step (e) and the intensity identified by the step (i);
k) summing the differential intensity to all target pixel intensities stored in said second memory;
l) detecting differential pixel intensities between the background pixel intensities stored in said first memory and corresponding target pixel intensities stored in said second memory; and
m) making a decision on said differential pixel intensities to produce an output signal representing presence or absence of said particles.

11. The method of claim 10, further comprising the steps of repeating the steps (f) to (m) by using the intensity of the group identified by the step (i) as the intensity of the group identified by the step (e), instead of the identified intensity of the group previously obtained from the background image of the step (b).

12. A method of detection particles generated within a semiconductor wafer process chamber, comprising the steps of:

a) emitting radiant energy of visible spectrum into said process chamber;

b) detecting a two-dimensional background image of scattered radiant energy within said process chamber before a wafer processing begins and producing a background video frame representing a matrix array of pixels of background intensities;

c) storing said matrix array of background pixel intensities in a first memory;

d) determining an average intensity of the background pixel intensities stored in the first memory;

e) detecting a two-dimensional target image of scattered radiant energy within said process chamber after said wafer processing begins and producing a target video frame representing a matrix array of pixels of target intensities;

f) storing said matrix array of target pixel intensities in a second memory;

g) determining an average intensity of the target pixel intensities stored in the second memory;

h) determining a differential intensity between the average intensities respectively determined by the steps (d) and (g);

i) summing the differential intensity to all target pixel intensities stored in said second memory;

j) detecting differential pixel intensities between the background pixel intensities stored in said first memory and corresponding target pixel intensities stored in said second memory; and k) making a decision on said differential pixel intensities to produce an output signal representing presence or absence of said particles.

13. The method of claim 10, further comprising the steps of repeating the steps (e) to (k) by using the average intensity of the step (g) as the average intensity of the step (d), instead of the average intensity previously obtained from the background image of the step (b).

* * * * *